United States Patent [19]

Leonard et al.

[11] Patent Number: 5,255,734
[45] Date of Patent: Oct. 26, 1993

[54] COMBINATION MOUNT AND FLUID PATH FOR HEAT EXCHANGER

[75] Inventors: Ronald J. Leonard; David B. Maurer, both of Ann Arbor; Erin J. Lindsay, Manchester, all of Mich.

[73] Assignee: Minnesota Mining and Manufacturing Company, St. Paul, Minn.

[21] Appl. No.: 888,840

[22] Filed: May 27, 1992

[51] Int. Cl.$^5$ .................... F28F 27/00; A61M 1/36
[52] U.S. Cl. .................... 165/96; 251/144; 422/46; 604/4; 604/113; 607/104
[58] Field of Search .............. 165/96, 76; 251/144, 251/149.9; 128/400, 401; 604/4, 113; 422/46

[56] References Cited

U.S. PATENT DOCUMENTS

| | | | |
|---|---|---|---|
| 3,315,734 | 4/1967 | Nadolny | 165/80 |
| 3,370,827 | 2/1968 | Stehlin | 251/144 |
| 3,585,995 | 6/1971 | Perkins et al. | 604/4 |
| 3,640,340 | 2/1972 | Leonard et al. | 165/166 |
| 4,047,563 | 9/1977 | Kurata | 165/158 |
| 4,065,264 | 12/1977 | Lewin | 23/258.5 |
| 4,138,288 | 2/1979 | Lewin | 195/1.8 |
| 4,138,464 | 2/1979 | Lewin | 422/46 |
| 4,351,355 | 9/1982 | Koller et al. | 251/144 |
| 4,735,775 | 4/1988 | Leonard et al. | 422/46 |
| 4,846,177 | 7/1989 | Leonard | 128/400 |
| 4,883,455 | 11/1989 | Leonard | 604/4 |
| 4,902,476 | 2/1990 | Gordon et al. | 422/46 |
| 5,120,501 | 6/1992 | Mathewson et al. | 422/46 |

FOREIGN PATENT DOCUMENTS

| | | |
|---|---|---|
| 2617208 | 7/1977 | Fed. Rep. of Germany . |
| 2719171 | 12/1977 | Fed. Rep. of Germany . |
| 2607707 | 6/1988 | France . |

OTHER PUBLICATIONS 3M trade literature "Plain and simple . . . ", 3M Form No. 78-8067-3788-4 (1991).
3M Technical Compendium, "SARNS Conducer Heat Exchanger", 3M Form No. 78-8067-3506-0 (1991).
3M trade literature folder, "When you bring efficiency to the surface . . . you can lower the prime." (includes 4 flyers).

Primary Examiner—Martin P. Schwadron
Assistant Examiner—L. R. Leo
Attorney, Agent, or Firm—Gary L. Griswold; Walter N. Kirn; Stephen W. Bauer

[57] ABSTRACT

A mounting assembly for holding a heat exchanger particularly of the type used in administering cardioplegia during heart surgery. The mounting assembly both mounts the heat exchanger and provides heatexchanging fluid (e.g., water) to the heat exchanger. The mounting assembly also includes a valve and sealing mechanism which are simultaneously operated to ensure that the valve is not opened until after the heat exchanger is properly sealed. The sealing mechanism includes an expandable seal that is designed to hold the heat exchanger on the mounting assembly.

43 Claims, 6 Drawing Sheets

COMBINATION MOUNT AND FLUID PATH FOR HEAT EXCHANGER

This invention relates generally to mounting devices and fluid path connectors, and more particularly to a combination mount and fluid path for a heat exchanger, such as a heat exchanger used to cool or heat blood and/or cardioplegia solution.

BACKGROUND OF THE INVENTION

Co-assigned U.S. Pat. No 4,846,177 discloses a combination fluid path and mount for heat exchangers, such as heat exchangers used to heat or cool blood and/or cardioplegia solution during heart surgery. That combination water path and mount is designed to mount heat exchangers having an inner surface defining a passageway in which heat-exchanging fluid (e.g., water) circulates. Heat exchangers of that general type are now available under the trade designation "SARNS CONDUCER" from the Minnesota Mining and Manufacturing Company, St. Paul, Minn. See, also, co-assigned U.S. Pat. No. 4,883,455.

That mount generally comprises a cylindrical body that is adapted to be received in the passageway for heat-exchanging fluid of the heat exchanger, and a bracket for mounting the body on a support. The body has heat-exchanging fluid inlet and outlet passageways, each opening through the circumference of the body for circulating the heat-exchanging fluid in the passageway of a heat exchanger. In that mount, a fixing-sealing means or mechanism has been provided for removably fixing the heat exchanger to the body and sealing between the body and the inner surface of the heat exchanger to prevent leakage of the heat-exchanging fluid. The fixing-sealing means works by expanding a portion of the periphery of the body against the inner surface of the heat exchanger to form a seal therebetween and to hold the heat exchanger on the body.

In that mount, hose fittings have been provided on the bracket and in fluid communication with the heat-exchanging fluid inlet and outlet passageways for connecting water inlet and outlet hoses. The "SARNS CONDUCER" brand mount does not include a valve for stopping the flow of heat-exchanging fluid through the mount. Water flow in that mount was controlled by manually shutting off the flow of water through the water inlet and outlet hoses.

SUMMARY OF THE INVENTION

The invention provides a mounting assembly that is adapted for holding a heat exchanger of the type having a passageway-defining surface defining at least a portion of a passageway through which heat-exchanging fluid is circulated. The invention provides a mounting assembly that is particularly adapted for mounting a heat exchanger of the type used to heat or cool fluid used in cardioplegia and providing heat-exchanging fluid (e.g., water) to the heat exchanger being mounted thereon; and which is adapted to open a valve to supply heat-exchanging fluid to the heat exchanger only after the heat exchanger is securely mounted on the mounting assembly and to close the valve to shut-off the supply of heat-exchanging fluid before the mounting assembly allows the heat exchanger to be removed from the mounting assembly. The mounting assembly is designed so that the valve is opened or closed as the user manually operates the mounting assembly to lock or release the heat exchanger.

Generally, a mounting assembly of the invention comprises a bracket for mounting the mounting assembly on a support, and a body mounted on the bracket. The body is adapted to be received in the passageway of the heat exchanger. The body includes heat-exchanging fluid inlet and outlet passageways for circulating heat exchanging fluid through the passageway of the heat exchanger. Fixing-sealing means is provided on the body and is movable between operating and releasing positions. In the operating position, the fixing-sealing means is adapted for sealing against the passageway-defining surface of the heat exchanger to seal the passageway of the heat exchanger and hold the heat exchanger on the body. In the releasing position, the fixing-sealing means is adapted for releasing the heat exchanger from the body to allow the heat exchanger to be removed from the mounting assembly or to be mounted on the mounting assembly. Valve means is also provided. The valve means is operatively linked with the fixing-sealing means, and is adapted for opening the heat-exchanging fluid inlet passageway when the fixing-sealing means is in its operating position, and closing the heat-exchanging fluid inlet passageway when the fixing-sealing means is in its releasing position.

Preferably, the fixing-sealing means has a non-operating, sealing position between the operating position and the releasing position. In the non-operating, sealing position, the fixing-sealing means is adapted for sealing against the passageway-defining surface of the heat exchanger to seal the passageway of the heat exchanger and hold the heat exchanger on the body but the valve means is closed to prevent the flow of heat-exchanging fluid in the heat-exchanging fluid inlet passageway.

Also, preferably, the mounting assembly is adapted for mounting a heat exchanger of the type having a generally cylindrical cavity defining the passageway for heat-exchanging fluid, and the body of the mounting assembly is elongate and generally cylindrical. The fixing-sealing means preferably comprises a ring-engaging surface on the body, an expandable annular sealing ring co-axial with the body and engaging the ring-engaging surface of the body, and a seal-actuating member mounted on the body and trapping the expandable annular sealing ring against the ring-engaging surface of the body. The seal-actuating member is movable as the fixing-sealing means is moved between its releasing position and its non-operating, sealing position from a first position, wherein the seal-actuating member does not press the sealing ring against the ring-engaging surface sufficiently to expand the sealing ring into sealing engagement with the passageway-defining surface of the heat exchanger, to a second position, wherein the seal-actuating member presses against the sealing ring sufficiently to squeeze the annular ring against the ring-engaging surface to expand the sealing ring into sealing engagement with the passageway-defining surface of the heat exchanger. The seal-actuating member is maintained in its second position as the fixing-sealing means is moved between its non-operating, sealing position and its operating position.

Conveniently, the mounting assembly further comprises cam means operatively linked with the sealactuating member to move the seal-actuating member between its first and second positions. For example, the cam means may comprise a cam surface mounted on the bracket, a cam follower adapted to engage the cam surface, a linking rod, one end of which is connected to the seal-actuating member and the other end of which is connected to the cam follower, and a spring for biasing the cam follower against the cam surface. The cam surface and cam follower are adapted for rotation relative to one another from the releasing position, through the non-operating, sealing position, to the operating position to move the sealactuating member between its first and second positions. The cam surface is configured to hold the seal-actuating member in its second position in and between the operating position and the non-operating, sealing position.

The mounting assembly preferably includes an adjustment means operatively associated with the linking rod for manually adjusting the first and second positions of the seal-actuating member. For example, the adjustment means may include an elongate slot formed in the linking rod adjacent the end connected to the cam follower and extending in the axial direction of the linking rod. The elongate slot receives the cam follower to connect the cam follower to the linking arm. An adjusting screw is threadably received in the linking rod, with one end of the adjusting screw engaging the cam follower to adjust the length of the linking rod between the cam follower and the seal-actuating member.

Also, preferably, the mounting assembly includes a fluid inlet and a fluid outlet in fluid communication with the valve means and having connection means for connecting to fluid supply and/or drain conduits, and the valve means includes bypass means for directing fluid flow directly to the outlet from the inlet while bypassing the heat-exchanging inlet and outlet passageways when the valve means is closed.

Other features will be pointed out hereinafter.

BRIEF DESCRIPTION OF THE DRAWING

The invention will be further described with reference to the drawing wherein corresponding reference characters indicate corresponding parts throughout the several views of the drawing, and wherein.

DETAILED DESCRIPTION OF A PREFERRED EMBODIMENT

Figure 1:
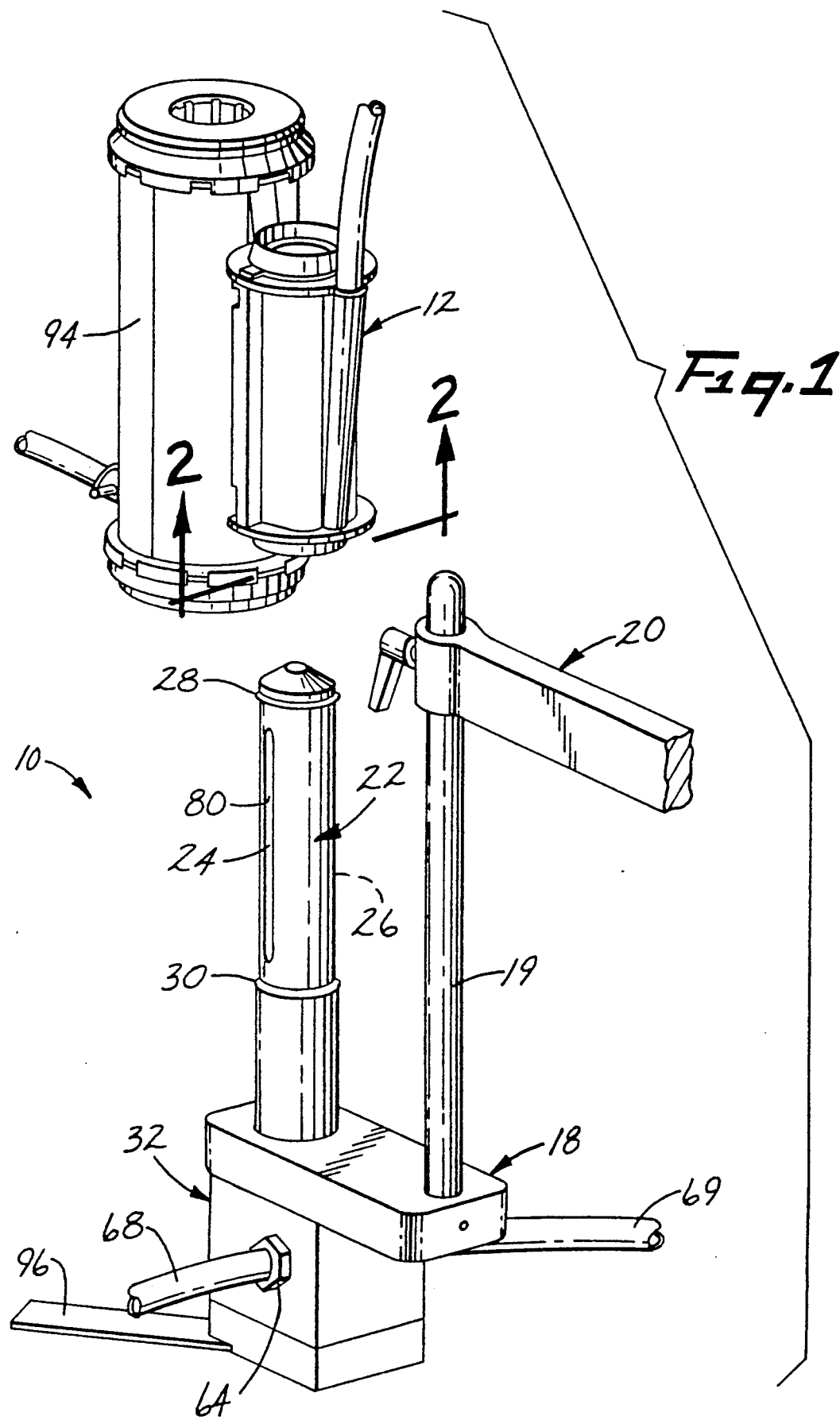
FIG. 1 is perspective view of the combination of the invention, showing a heat exchanger/blood oxygenator of the combination separated from the mounting assembly of the invention.
Figure 2:
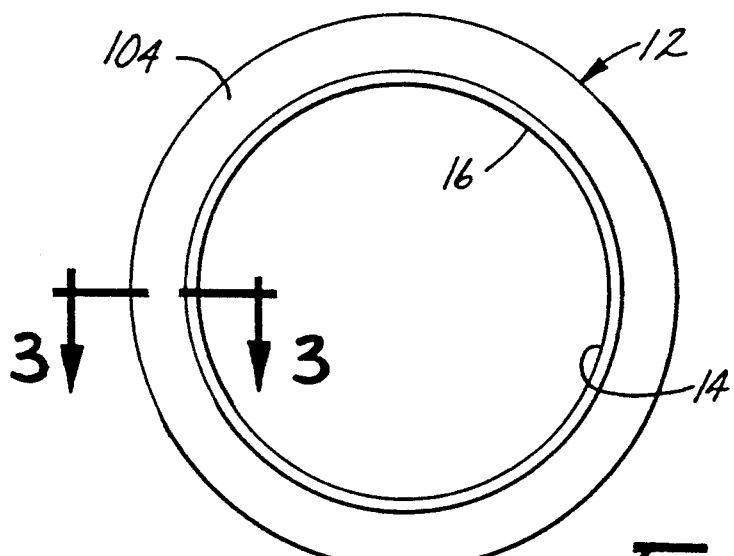
FIG. 2 is a bottom view of the heat exchanger taken along direction 2—2 of FIG. 1.

Now referring to the drawings, a mounting assembly of the invention will be designated in its entirety by the reference numeral 10. The mounting assembly 10 is adapted to hold a heat exchanger generally designated 12 of the type having a passageway-defining surface 14 defining at least a portion of a generally cylindrical passageway 16 through which heat-exchanging fluid is circulated. Co-assigned U.S. Pat. Nos. 4,846,177 and 4,883,455 describe among other things mounting assemblies and heat exchangers, and are incorporated herein by reference.

The mounting assembly 10 is particularly designed to hold heat exchangers 12 of the type used to cool or heat blood or solution for cardioplegia and for supplying heat-exchanging fluid (e.g., water) to the heat exchanger 12 so that heat may be transferred between the blood or solution and the heat-exchanging fluid. The mounting assembly 10 provides a mechanism for quickly connecting and disconnecting heat exchangers 12, which in the case of cardioplegia must be sterile and may be disposable, to the mounting assembly 10, which may be reusable.

As shown in FIG. 1, the mounting assembly 10 generally comprises a bracket 18 for mounting the mounting assembly 10 on a support, such as a clamp 20, and a generally cylindrical, elongate body 22 mounted on the bracket 18. The body 22 is adapted to be received in the passageway 16 of the heat exchanger 12. The body 22 includes heat-exchanging fluid inlet and outlet passageways 24 and 26 for circulating heat exchanging fluid through the passageway 16 of the heat exchanger 12. An elongate pole 19 may be provided on the bracket 18 to provide a suitable structure for the clamp 20 to lock onto.

Figure 4:
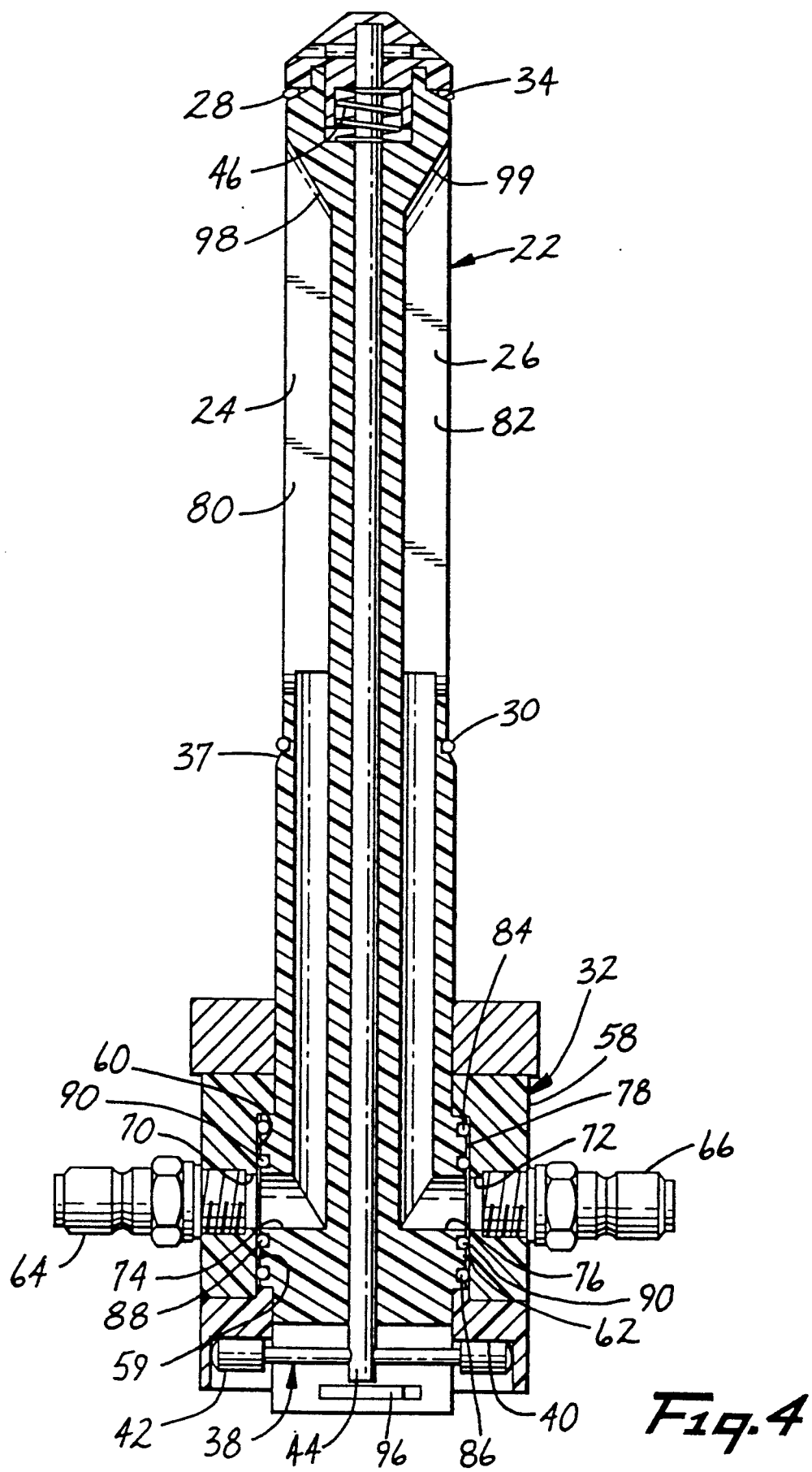
FIG. 4 is a longitudinal cross-sectional view of the mounting assembly of the invention in its operating position, in which the mounting assembly would hold and seal against the heat exchanger (not shown in the figure) and the valve is open.
Figure 5:
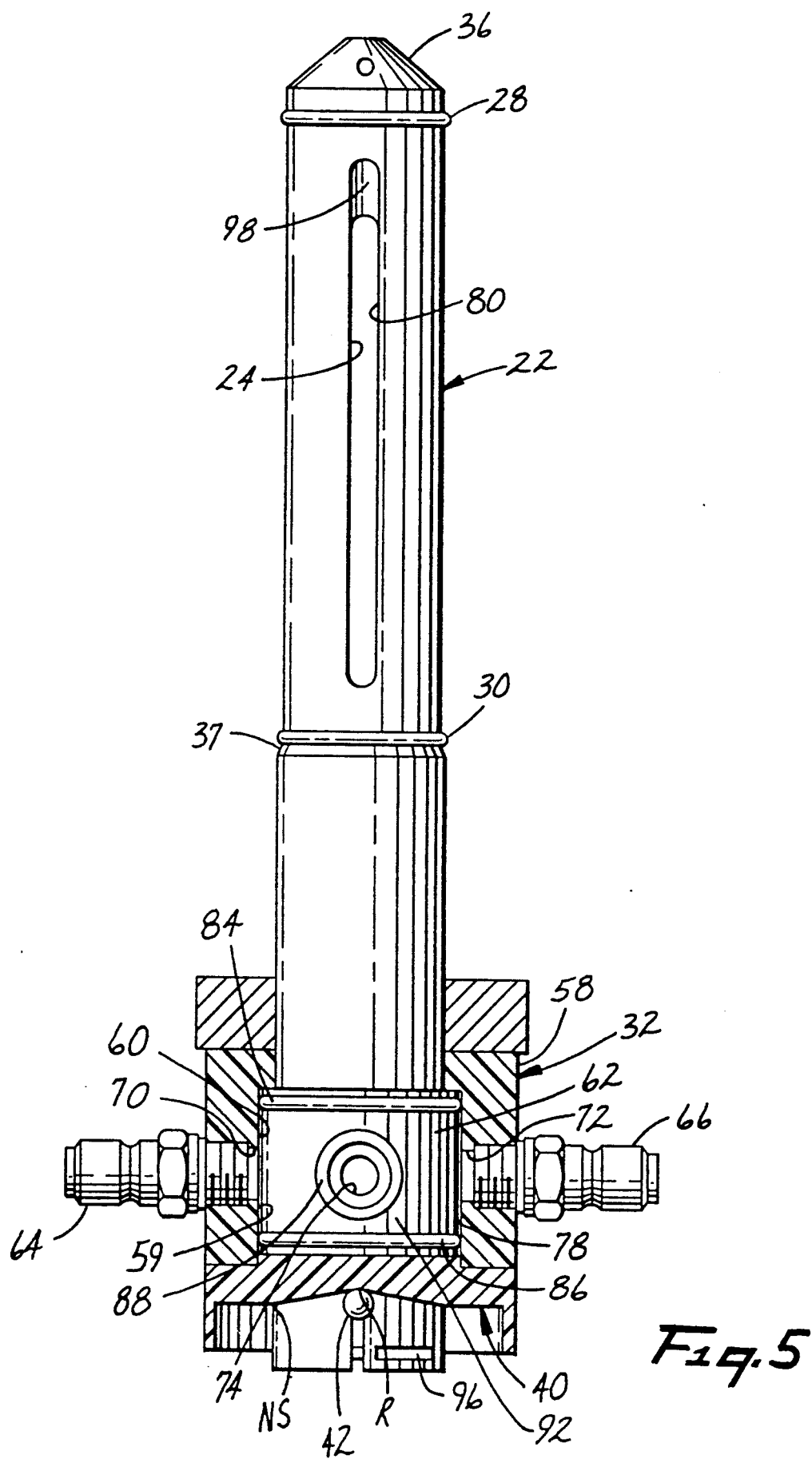
FIG. 5 is a side view of the mounting assembly similar in some respects to FIG. 4 with the valve shown in cross section, illustrating the releasing position in which a heat exchanger can be placed on or removed from the mounting assembly and the valve is closed.

Fixing-sealing means (e.g., including first and second sealing O-rings 28 and 30) is provided on the body 22. The fixing-sealing means (at 28) is movable between operating and releasing positions (FIGS. 4 and 5, respectively). In the operating position (FIG. 4), the fixing-sealing means (at 28) is adapted for sealing against the passageway-defining surface of the heat exchanger to seal the passageway 16 of the heat exchanger 12 and hold the heat exchanger 12 on the body 22. In the releasing position (FIG. 5), the fixing-sealing means (at 28) is adapted for releasing the heat exchanger 12 from the body 22 to allow the heat exchanger 12 to be removed from the mounting assembly 10 or to be mounted on the mounting assembly 10. The sealing rings 28 and 30 may be formed of silicone rubber material, preferably with the first sealing ring 28 having a durometer of approximately 40 on the Shore A scale, and the second sealing ring 30 having a durometer of approximately 70 on the Shore A scale.

Valve means generally designated 32 is operatively linked with the fixing-sealing means 28 to open the heat-exchanging fluid inlet passageway 24 when the fixing-sealing means 28 is in its operating position (FIG. 4), and closing the heat-exchanging fluid inlet passageway 24 when the fixing-sealing means 28 is in its releasing position (FIG. 5). Preferably, the valve means 32 includes means for opening and closing the heat-exchanging fluid outlet passageway 26 when the heat-exchanging fluid inlet passageway 24 is opened or closed, respectively. One embodiment of the valve means 2 will be described in more detail below.

Preferably, the fixing-sealing means 28 further has a non-operating, sealing position (FIG. 6) between the operating position (FIG. 4) and the releasing position (FIG. 5). In the non-operating, sealing position (FIG. 6), the fixing-sealing means 28 is adapted for sealing against the passageway-defining surface 14 of the heat exchanger 12 to seal the passageway 16 of the heat exchanger 12 and hold the heat exchanger 12 on the body 22 but the valve means 32 is closed to prevent the flow of heat-exchanging fluid in the heat-exchanging fluid inlet passageway 24 (and most preferably to close the heat-exchanging fluid outlet passageway 26 as well).

Preferably, the fixing-sealing means (at 28) comprises a ring-engaging surface 34 on the body 22, the expandable annular "first" sealing ring 28; and a seal-actuating member 36 mounted on the body 22, trapping the first sealing ring 28 against the ring-engaging surface 34 of the body 22. The first sealing ring 28 is co-axial with the body 22, and engages the ring-engaging surface 34 of the body 22. The ring-engaging surface 34 may be positioned axially along the body 22 between the first sealing ring 28 and the second seal 30, and the seal-actuating member 36 may be positioned axially of the first sealing ring 28 in the direction away from the second seal 30.

Figure 6:
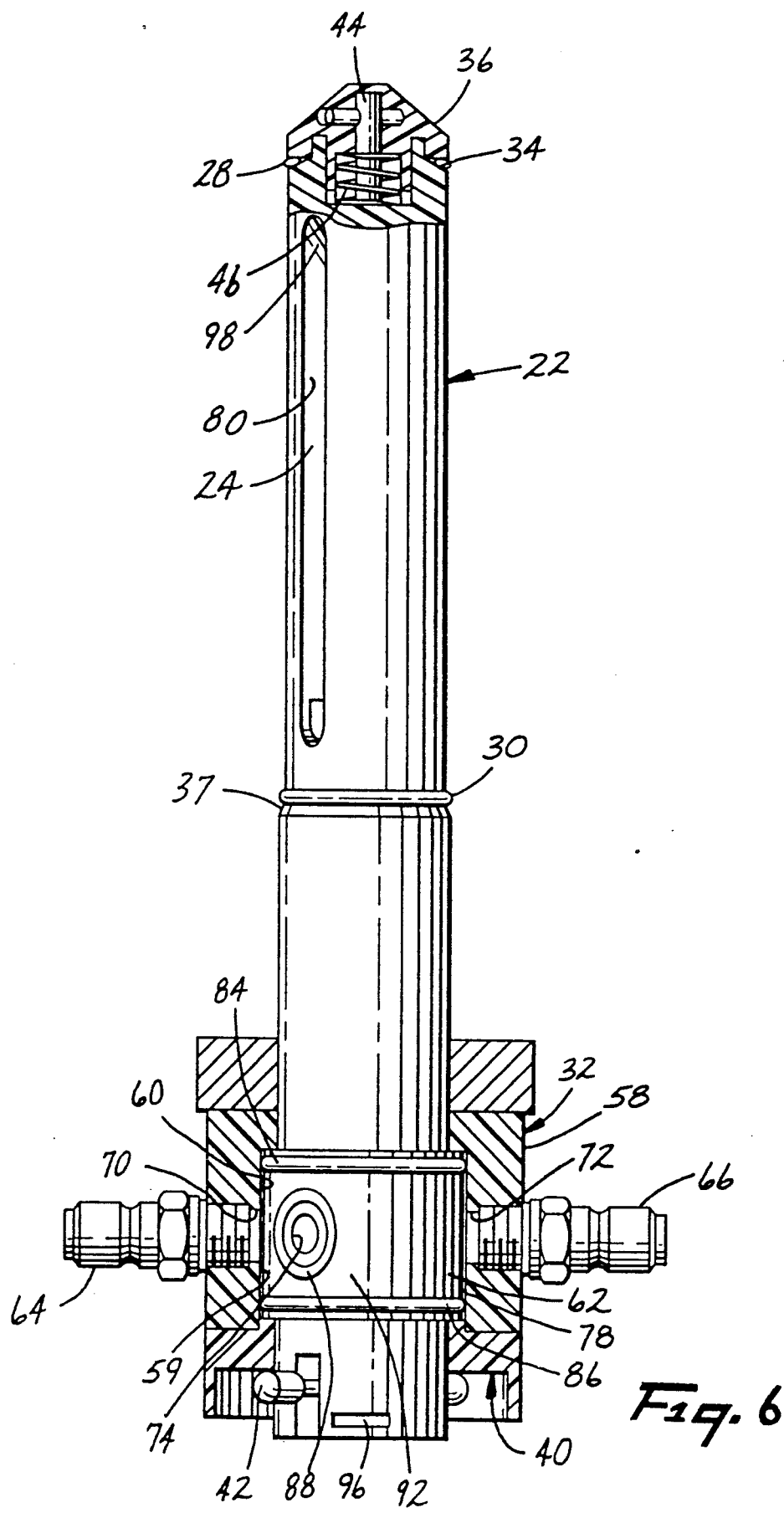
FIG. 6 is a side view of the mounting assembly similar in some respects to FIGS. 4 and 5 with portions in cross section, illustrating the non-operating sealing position in which the mounting assembly would hold and seal against the heat exchanger but the valve would be closed.

The seal-actuating member 36 is movable from a first position (FIG. 5) to a second position (FIGS. 4 and 6) as the fixing-sealing means is moved between its releasing position (FIG. 5) and its non-operating, sealing position (FIG. 6). In the first position (FIG. 5), the seal-actuating member 36 does not press the first sealing ring 28 against the ring-engaging surface 34 sufficiently to expand the sealing ring 28 into sealing engagement with the passageway-defining surface 14 of the heat exchanger 12. Most preferably the sealactuating member 36 does not squeeze the first sealing ring 28 against the seal-engaging surface 34 at all when in its first position.

In the second position (FIGS. 4 and 6), the seal-actuating member 36 presses against the first sealing ring 28 sufficiently to squeeze the first sealing ring 28 against the ring-engaging surface 34 to expand the first sealing ring 28 into sealing engagement with the passageway-defining surface 14 of the heat exchanger 12. As illustrated in the figures, the seal-actuating member 36 is movable from its first position (FIG. 5) to its second position (FIG. 4) in the direction toward the second seal 30 (downwardly in FIGS. 4–6).

The seal-actuating member 36 is maintained in its second position (FIGS. 4 and 6) as the fixing-sealing means is moved between its non-operating, sealing position (FIG. 6) and its operating position (FIG. 4). Maintaining the seal-actuating member 36 in its second position in and between the non-operating, sealing position (FIG. 6) and the operating position (FIG. 4) ensures that the sealing ring 28 and second seal 30 are kept in sealing engagement with the passageway-defining surface 14 of the heat exchanger 12 when the valve means 32 is open and as it is opened and closed. Only after the valve means 32 is closed, e.g., between the non-operating, sealing position (FIG. 6) and the releasing position (FIG. 5), does the seal-actuating member 36 move to its first position to release the sealing ring 28 from the passageway-defining surface 14 of the heat exchanger 12.

As illustrated in FIG. 4, the first and second seals 28 and 30 are mounted on the body 22 and are spaced apart axially along the body 22 from one another a suitable distance relative to the length of the heat-exchanging passageway 16 of the heat exchanger 12 that is to be mounted on the mounting assembly 10. Most preferably, the length of the heat-exchanging passageway 16 and the distance between the first and second seals are approximately the same (e.g., approximately 6 inches (152 mm)). This arrangement allows the second seal 30 to sealingly engage the passageway-defining surface 14 of the heat exchanger 12 adjacent one end of the passageway-defining surface 14, and the first seal 28 to sealingly engage the passageway-defining surface 14 adjacent the other end, with the heat-exchanging fluid thereby being prevented from leaking from the ends of the heat-exchanging fluid passageway 16.

Most preferably, suitable means is provided for moving the expandable first sealing ring 28 axially toward the second seal 30 as the first sealing ring 28 is moved/expanded to its second position (FIG. 4) from its first position (FIG. 5). For example, the ring-engaging surface 34 may be generally conical, tapering outwardly in the direction toward the second seal 30, so that the first sealing ring 28 is pushed axially toward the second seal 30 when it is pressed against the seal-engaging surface 34 by the seal-actuating member 36. The angle of taper of the ring-engaging surface 34 may conveniently be approximately 60 degrees. As used herein, "angle of taper" refers to the angle formed between the ring-engaging surface 34 relative to the longitudinal axis of the body 22. This combined axial motion and expansion of the first sealing ring 28 is believed to help secure the heat exchanger 12 on the mounting assembly and to maintain a reliable seal against the passageway-defining surface 14 of the heat exchanger 12. It drives the heat exchanger 12 a short distance axially along the body 22 of the mounting assembly i0 against the second seal 30.

As illustrated in FIG. 5, for example, the annular diameter of the second seal 30 is preferably greater than the diameter of the first seal 28 when the first seal 28 is in its first or unexpanded position. As used herein with reference to O-ring seals, "annular" diameter refers to the large diameter of the O-ring about its axis of symmetry (e.g., the longitudinal axis of the elongate body 22), as opposed to the "cross-sectional" diameter which refers to the relatively smaller diameter of a cross section of a portion or the O-ring. The arrangement is such that as the first seal 28 is expanded and moved toward the second seal 30 as described above, the first seal 28 pushes the heat exchanger 12 toward the second seal 30 to form a seal between the second seal 30 and the passageway-defining surface 14 of the heat exchanger 12 without requiring expansion of the second seal 30. The first and second sealing O-rings 28 and 30 preferably have circular cross sections, although other cross sections could be used.

The second seal 30 is preferably held in an annular channel (at 30) formed in the body 22, and is most preferably backed up with an annular shoulder 37 to prevent the second seal 30 from being rolled out of its annular channel 30 as the heat exchanger 12 is pushed against the second seal 30 by the axial motion of the first seal 28. The shoulder 37 may have be tapered at an angle of approximately 24 degrees with respect to the longitudinal axis of the body 22.

As an alternative to the generally stationary second seal 30 of the preferred embodiment, a second seal (not shown) could be provided with an actuating mechanism similar in some respects to the seal-actuating member 36 used with the first seal 28. Such an actuating mechanism in the case of the second seal would be arranged to move the second seal axially toward the first seal as the second seal is expanded. The contemplated alternative arrangement would be such that the distance between the two seals would be reduced as the seals are expanded to their second (expanded, sealing) positions to securely hold the heat exchanger 12 between them.

In yet another alternative embodiment, the distance between the first and second seals could be increased as the seals are moved to their second (expanded, sealing) position(s), and the passageway-defining surface of the corresponding heat exchanger could be provided with annular shoulders (not shown). In such an alternative embodiment, the first and second seals would apply force against the annular shoulders to hold the heat exchanger on the alternative mounting assembly (not shown).

Figure 3:
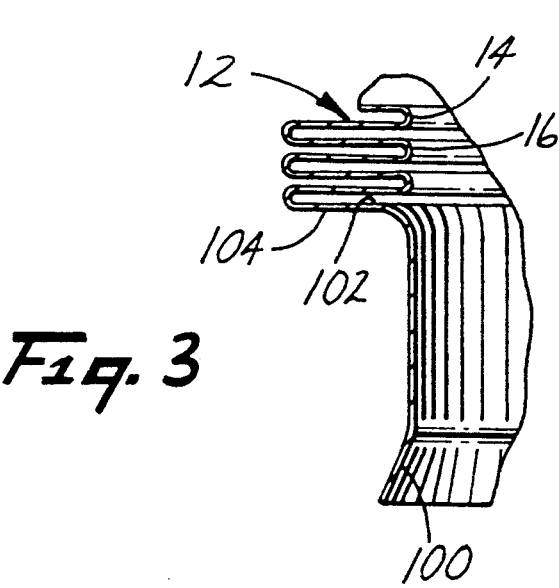
FIG. 3 is a cross-sectional view of the heat exchanger taken substantially along line 3—3 of FIG. 2.
Figure 9:
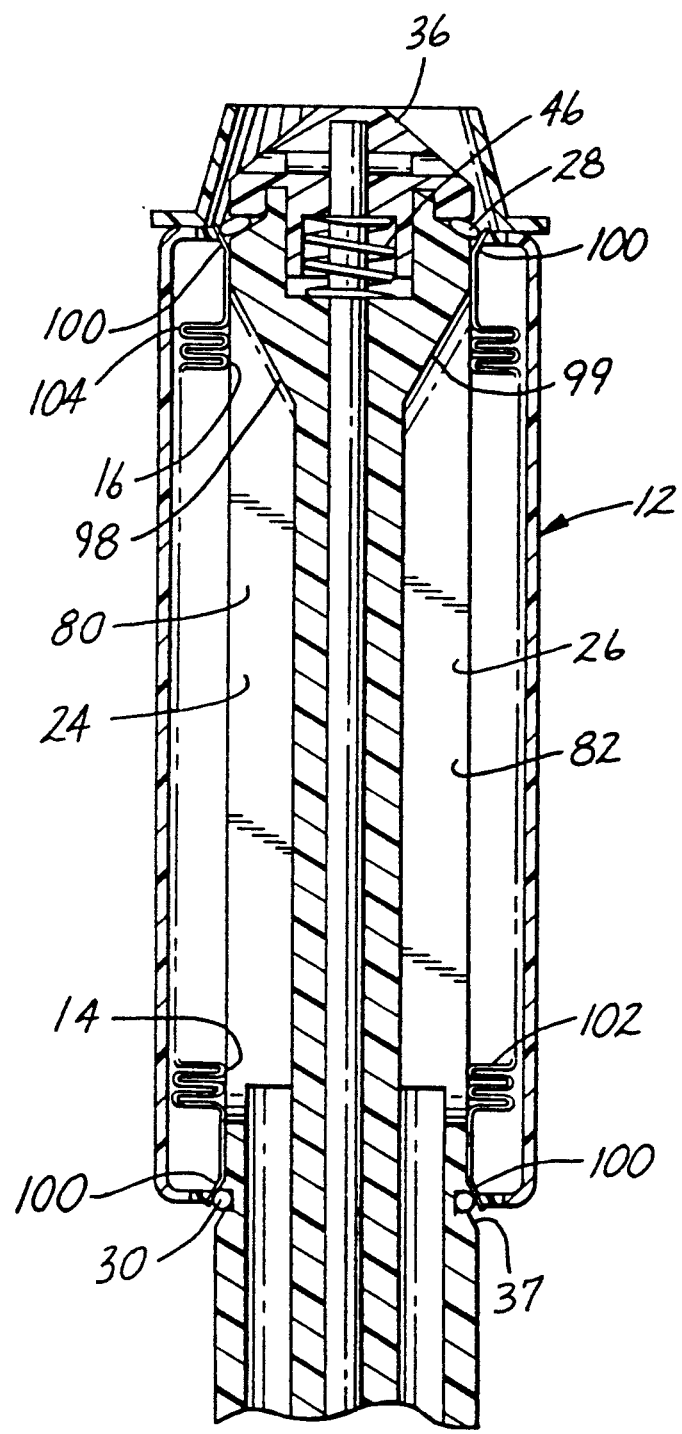
FIG. 9 is a cross sectional view of a portion of the mounting assembly and the heat exchanger showing the cooperation of the flared flanges of FIG. 3 of the heat exchanger relative to the fixing-sealing means of FIGS. 1 and 4–6.

As illustrated in FIGS. 3 and 9, each end of the passageway-defining surface 14 of the heat exchanger 12 may be in the form of a flared flange 100. The flange 100 is most preferably flared at an angle of approximately 24 degrees with respect to the longitudinal axis of the passageway 16. As the first sealing ring 28 engages one of the flanges 100, the first sealing ring 28 applies an axially directed force component (in addition to a radially outwardly directed force component) to the flange 100, with the result that the heat exchanger 12 is moved axially relative to the second seal 30 such that a sealing force is applied between the second seal 30 and the other flared flange 100. It is contemplated that the flared flange 100 of the heat exchanger 12 could also be used with alternate embodiments of the mounting assembly 10, in which the first sealing ring (not shown) does not move axially as it is expanded to its second (sealing) position.

Also, as illustrated in FIG. 3, the passageway-defining surface 14 of the heat exchanger 12 is most preferably an undulating surface, defining a plurality of channels through which heat exchanging fluid (e.g., water) flows in close proximity to the surface 14. This arrangement is believed to be helpful with respect to maximizing heat transfer through the surface 14. The surface 104 of the barrier 102 opposite the passageway-defining surface 14 is in contact with the blood and/or cardioplegia solution. That surface 104 is also undulating, defining channels for the flow of blood and/or cardioplegia solution along the surface 104.

Preferably, cam means generally designated 38 is operatively linked with the seal-actuating member 36 to move the seal-actuating member 36 between its first and second positions. For example, a cam surface 40 and cam follower 42 can be provided/mounted on the bracket 18. The cam follower 42 is adapted to engage the cam surface 40 to move the seal-actuating member 36 between its first and second positions as the cam follower 42 moves (e.g., rotates) relative to the cam surface 40. The cam follower 42 preferably includes rollers (also at 42) adjacent its ends in rolling engagement with the cam surface 40. The arrangement is such that the rollers turn around the longitudinal axis of the cam follower 42 as the cam follower 42 is rotated around the longitudinal axis of the body 22 between the releasing, non-operating, sealing and operating positions.

A linking rod 44 operatively links the cam means 38 to the seal-actuating member 36. One end of the linking rod 44 is connected to the seal-actuating member 36, and the other end of the linking rod 44 is connected to the cam follower 42 so that the seal-actuating member 36 and cam follower 42 move, at least in the axial direction (relative to the body) in tandem.

A steel coil spring 46, conveniently engaging the seal-actuating member 36 and the body 22, biases the cam follower 42 against the cam surface 40. The spring 46 is illustrated in the drawing as biasing the sealactuating member 36 to its first position (not expanding the first sealing ring 28), which is the preferred arrangement, and the seal-actuating member 36 is moved against that spring bias to its second position (expanded first sealing ring 28) by movement of the cam follower 42 along the cam surface 40.

The cam follower 42 could alternatively be biased against the cam surface 40 by a spring (not shown) directly engaging the cam follower 42. Also, alternately, a spring (not shown) could be provided that would bias the seal-actuating member 36 to its second position, and the cam surface 40 and cam follower 42 could be configured and arranged to move the seal-actuating member 36 to its second position against the spring bias. Other alternatives include providing a cam slot (not shown) in place of the cam surface 40 for positively guiding a cam follower (not shown) to move the seal-actuating member 36 between its first and second positions without the use of a spring to bias it to one of those positions.

Figure 7:
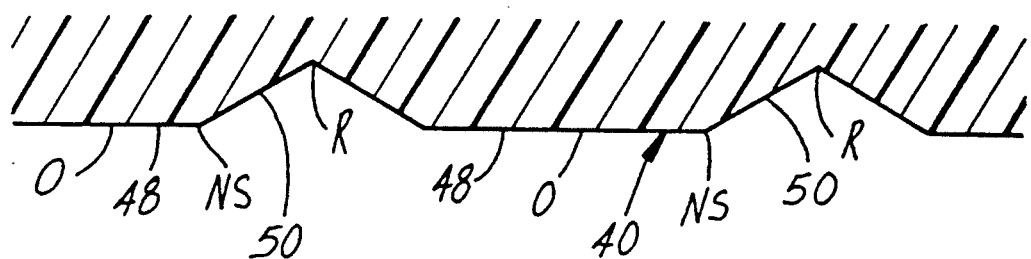
FIG. 7 is an enlarged unwrapped profile of the cam surface.

In the preferred embodiment, the cam surface 40 is configured to hold the seal-actuating member 36 in its second position (FIGS. 4 and 6) in and between the operating position (FIG. 4) and the non-operating, sealing position (FIG. 6). A suitable contour of the cam surface 40 controlling motion of the cam follower 42 and seal-actuating member 36 is illustrated in FIG. 7. The contour of the cam surface 40 is generally flat as indicated at 48 between points "O" and "NS", which is the portion 48 of the cam surface 40 engaging the cam follower 42 in and between the operating ("O") position and the non-operating, sealing ("NS") position. At this portion 48 of the cam surface 40, the cam follower 42 is engaged by the cam surface 40 to hold the seal-actuating member 36 against the bias of spring 46 to the second position (thereby expanding first sealing ring 28).

The contour of the cam surface 40 is generally sloped as indicated at 50 (FIG. 7) between points "NS" and "R", which is the portion 50 of the cam surface 40 engaging the cam follower 42 between the non-operating, sealing ("NS") position and the releasing ("R") position. At this sloped portion 50 of the cam surface 40, the cam follower 42 is engaged by the cam surface 40 as the cam follower 42 is rotated from point "R" to point "NS" to pull the seal-actuating member 36 to its second position (to expand the first sealing ring 28). When the cam follower 42 is rotated along the sloped portion 50 from point "NS" to point "R", the spring 46 is allowed to move the seal-actuating member 36 to its first position (so as not to expand the first sealing ring 28).

Figure 8:
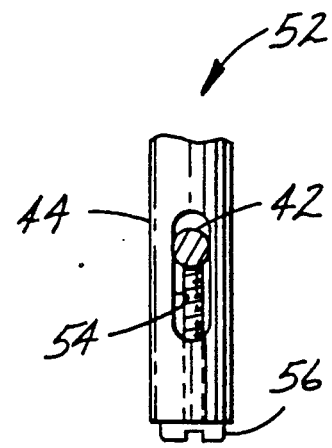
FIG. 8 is an enlarged cross-sectional view in FIG. 4, illustrating an adjustment mechanism.

As illustrated in FIG. 8, an adjustment means generally designated 52 may be provided for manually adjusting the first and second positions of the sealactuating member 36. The adjustment means 52 comprises an elongate slot 54 formed in the linking rod 44 adjacent the end connected to the cam follower 42 and extending in the axial direction of the linking rod 44. The elongate slot 54 receives the cam follower 42 to connect the cam follower 42 to the linking arm 44. An adjusting screw 56 is threadably received in the linxing rod 44, with one end of the adjusting screw 56 engaging the cam follower 42 to adjust the length of the linking rod 44 between the cam follower 42 and the seal-actuating member 36.

By turning the adjusting screw 56, the distance between the cam follower 42 and the seal-actuating member can be adjusted either to increase or decrease the amount of compression applied to the first sealing ring 28 in the axial direction. This allows some fine tuning to ensure that the first sealing ring 28 securely seals against the passageway-defining surface 14 of the heat exchanger 12 when the seal-actuating member 36 is in its second position, on the one hand, and that the first sealing ring 28 releases the heat exchanger 12 when the seal-actuating member 36 is in its first position, on the other hand.

Preferably, the valve means 32 generally comprises a valve housing 58 having a wall 59 defining a generally cylindrical cavity 60, and a cylindrical valve member 62 mounted in the cavity 60 for rotation relative the valve housing 58. Connection means, designated 64 and 66, is provided for connecting the valve housing 58 to fluid supply and drain conduits 68 and 69. The connection means 64, 66 may take the form of two quick-disconnect type hose connections 64 and 66 of conventional design, which are mounted in fluid communication with fluid inlet and outlets 70 and 72 opening into the cylindrical cavity 60 of the valve housing 58. Most preferably, the fluid inlet and outlet 70 and 72 open into the cavity 60 through opposite sides of the cavity-defining wall 59 as illustrated in FIGS. 4-6, and the connections 64 and 66 are mounted on opposite sides of the valve housing 58.

The valve member 62 has fluid passageways 74 and 76 opening through the circumferential surface 78 of the valve member 62 in fluid communication with the heat-exchanging fluid inlet and outlet passageways 24 and 26. Most preferably, the valve member 62 is integrally formed (e.g., molded) with the body 22 of the mounting assembly 10, with the fluid passageways 74 and 76 constituting extensions of the heat-exchanging fluid inlet and outlet passageways 24 and 26. The arrangement is such that the heat-exchanging fluid inlet and outlet passageways 24 and 26 extend generally longitudinally through the body 22 between their openings 80 and 82 through opposite sides of the body 22 and the fluid passageways 74 and 76, which extend laterally/radially outwardly to the circumferential surface 78 of the valve member 62 and open through opposite sides of that circumferential surface 78.

Most preferably, the body 22 and valve member 62 are "integrally" molded of suitable plastic material, such as polyurethane having a durometer of approximately 75 on the Shore D scale. As used herein. "integrally" refers to an integral one-piece construction formed, for example, by molding or machining as opposed to two pieces mechanically fastened together.

The valve member 62 is rotatable relative to the valve housing 58 between an open position (FIG. 4) and a closed position (FIGS. 5 and 6). In the open position (FIG. 4), the openings (at 74 and 76) of the fluid passageways 74 and 76 in the valve member 62 are aligned with the openings (at 70 and 72) of fluid inlet and outlet 70 and 72 in the valve housing 58 so that the fluid inlet and outlet 70 and 72 are in fluid communication with the heat-exchanging fluid inlet and outlet passageways 24 and 26. In the closed position (FIGS. 5 and 6), the openings (at 74 and 76) of the fluid passageways 74 and 76 in the valve member 62 are not aligned with the openings (at 70 and 72) of the fluid inlet and outlet 70 and 72 in the valve housing 58 such that heat-exchanging fluid inlet and outlet passageways 24 and 26 are not in fluid communication with the fluid inlet and outlet 70 and 72.

The arrangement of the openings (at 70, 72, 74 and 76) in the valve member 62 and valve housing 58 is such that fluid is provided to and drained from the heatexchanging fluid passageways 24 and 26 only when the valve member 62 is rotated to its open position (FIG. 4). The heat-exchanging fluid passageways 24 and 26 are closed to fluid flow by the valve member 62 when it is in its closed position(s) (FIGS. 5 and 6).

The valve member 62 is most preferably provided with a plurality of O-ring seals 84, 86, 88 and 90 for sealing between the valve member 62 and the cavity-defining wall 59. Two of these O-ring seals 84 and 86, constituting "major" seals, are received in two circumferentially extending seal-receiving channels (at 84 and 86) formed in the circumferential surface 78 of the valve member 62 and extending generally circumferentially around the valve member 62. O-ring seals 88 and 90, constituting "minor" seals, are received in two annular seal-receiving channels (at 88 and 90) in the circumferential surface 78 of the valve member 62 concentric with the radial openings of the fluid passageways 74 and 76. As used herein, "minor" seal and "major" seal is merely a short hand label referring to their relative size as represented in the drawing.

The minor seals 88 and 90 are provided around the openings (at 74 and 76) of the fluid passageways 74 and 76 to seal against the cavity-defining wall 59 of the valve housing 58. The fluid passageway openings 74 and 76 may have a diameter of approximately 0.375 inches (9.5 mm), and the minor seals 88 and 90 may have an annular diameter of approximately 0.715 inches (18 mm).

The minor seals 88 and 90 prevent leakage of fluid when the fluid passageway openings 74 and 76 are aligned with the inlet and outlet 70 and 72 (i.e., when the valve member 62 is in its open position (FIG. 4)). The minor seals 88 and 90 also ensure that fluid is not allowed to enter the fluid passageways 74 and 76 when the fluid passageway openings (at 74 and 76) are not aligned with the inlet and outlet 70 and 72 (i.e., when the valve member is in its closed position (FIGS. 5 and 6)). This prevents leakage from the heat-exchanging fluid passageways 24 and 26 both when a heat exchanger 12 is not mounted on the mounting assembly 10 and before the fixing sealing means is moved to its operating position (FIG. 4.

The major seals 84 and 86 are adapted to seal between the valve member 62 and the cavity-defining wall 59 along opposite sides of the fluid passageways 74 and 76, fluid inlet 70 and fluid outlet 72. That is, the "first" major seal 84 is positioned longitudi,nally relative to the body 22/valve member 62 on one side of the passageways 74, 76, inlet 70 and outlet 72, and the "second" major seal 86 is positioned longitudinally relative to the body 22/valve member 62 on the opposite side of the passageways 74, 76, inlet 70 and outlet 72.

The major seals 84 and 86 conveniently form an annular fluid bypass channel 92 between the circumferential surface 78 of the valve member 62 and the cavity-defining wall 59 of the valve housing 58. The bypass channel 92 brings the fluid inlet and outlet 70 and 72 into fluid communication with one another when the valve member 62 is in its closed position(s) (FIGS. 5 and 6) while bypassing the fluid passageways 74 and 76 and heat-exchanging fluid inlet and outlet passageways 24 and 26. A fluid bypass channel may alternatively be formed by an annular depression in the circumferential surface 78 of the valve member 62. The bypass channel 92 constitutes a preferred embodiment of a bypass means for directing fluid flow directly to the outlet 72 from the inlet 70 while bypassing the heat-exchanging inlet and outlet passageways 24 and 26 when the valve means 32 is closed.

As illustrated in FIG. 4, the heat-exchanging fluid inlet and outlet passageways 24 and 26 open outwardly through elongate openings 80 and 82 along opposite sides in the circumferential surface of the body 22. The elongate openings 80 and 82 are most preferably sufficiently long to cover most or the distance between O-rings 28 and 30 (e.g., −5 inches (127 mm) where the distance between O-rings 28 and 30 is 6 inches (152 mm)). This arrangement allows the elongate openings 80 and 82 to distribute heat-exchanging fluid more efficiently along substantially the entire length of the heat-exchanging surface 14 of the heat exchanger 12. The elongate openings 80 and 82 preferably have a width of approximately 0.250 inches (6 mm). As illustrated in FIG. 4, the ends 98 and 99 of the heat-exchanging fluid passageways 24 and 26 are preferably tapered, for example, at an angle of taper of 45 degrees.

The mounting assembly 10 of the invention is particularly designed for mounting a heat exchanger 12 of the type combined with a blood oxygenator 94 of otherwise conventional design. The combined heat exchanger 12/blood oxygenator 94 are operatively interconnected so that blood and/or blood/cardioplegia solution are cooled, for example, in the heat exchanger first and then passed through the blood oxygenator 94.

A handle 96 is preferably provided for manually moving the valve 32 and fixing-sealing means (e.g., sealactuating member 36 and first seal 28) between the releasing position, non-operating, sealing position and operating position. For example, the handle 96 may be mounted on the integral body 22/valve member 62 for rotating the valve member 62 relative to the valve housing 58 and rotating the cam follower 42 relative to the cam surface. Two notches (not shown) are preferably provided in the valve housing 58 for releasably holding the handle 96 in the releasing and operating positions. The handle 96 may be formed of steel which is both fairly rigid and sufficiently flexible and resilient to allow the handle 96 to be flexed to release it from the notches. A notch is not recommended for the non-operating, sealing position, since that position is merely a transition point between the releasing and operating positions.

OPERATION

Water may first be supplied to the mounting assembly 10 by connecting conduits 68 and 69 to the connections 64 and 66 with the mounting assembly 10 in its releasing position (FIG. 5), the valve means 32 in its closed position (also FIG. 5), and the first seal 28 in its first (unexpanded) position (also FIG. 5). The invention allows the supply conduit 68 to be supplied with water before mounting the heat exchanger 12 on the mounting assembly 12 and after releasing the heat exchanger. That is, water can be supplied to the supply conduit 68 once both conduits 68 and 69 have been connected to the connections 64 and 66.

The heat exchanger 12 is then placed on the body 12 of the mounting assembly 10, with the body 12 received in the passageway 16 of the heat exchanger 12. The cylindrical configuration of the passageway 16 of the heat exchanger 12 and body 22 of the mounting assembly 10 allow the heat exchanger 12 to be manually rotated on the body 22 until the orientation desired by the perfusionist is obtained.

The handle 96 is then moved to rotate the cam follower 42 relative to the cam surface 40 between the initial releasing position (FIG. 5) of the mounting assembly 10 through its non-operating, sealing position (FIG. 6) to the operating position (FIG. 4). The contour of the cam surface 40 causes the seal-actuating member 36 to squeeze the first seal 28 to its second (expanded) position as the handle 96 is rotated from the releasing position (FIG. 5) to the non-operating sealing position (FIG. 6), at which point the ends of the passageway 16 of the heat exchanger 12 are effectively sealed. This seal between the body 22 of the mounting assembly 10 and the heat exchanger 12 is maintained as the handle 96 is further rotated to the operating position (FIG. 4).

It has been found that the heat exchanger 12 can be manually rotated relative to the body 22 of the mounting assembly 10 when the mounting assembly 10 is in its operating position to re-orient the heat exchanger 12 without losing the seal between the heat exchanger 12 and the mounting assembly 10.

Moving the handle 96 from the releasing position (FIG. 5) through the non-operating, sealing position (FIG. 6) to the operating position (FIG. 4) as described above simultaneously manipulates the valve 32 to open the valve 32 after the ends of the passageway 16 of the heat exchanger 12 are sealed. The valve 32 is not opened too early (before sealing the ends of the passageway 16 of the heat exchanger 12). This is because the valve member 62 is rotated as the cam follower 42 is rotated, with the arrangement being such that the fluid passageway openings 74 and 76 of the valve member 62 are not brought into fluid communication with the inlet and outlet 70 and 72 of the valve housing 58 until after the first seal 28 is expanded to its second position (FIGS. 6 and 4). Before the valve 32 is opened, the bypass channel 92 allows the fluid to bypass the heat-exchanging fluid passageway 24 and 26 and run directly from the inlet 70 to the outlet 72 and drain into the drain conduit 69.

In order to remove the heat exchanger 12 from the mounting assembly 10, the handle 96 is simply rotated from the operating position (FIG. 4) to the releasing position (FIG. 5) and the heat exchanger 12 can be removed. Breaking down this operation into its parts, it can be seen that the valve 32 is closed before the expandable seal 28 is allowed to move from its second position (FIGS. 4 and 6) toward its first position (FIG. 5). This is because as tne handle 96 is manually rotated from the operating position (FIG. 4) toward the non-operating, sealing position (FIG. 6), the fluid passageways 74 and 76 of the valve member 62 are taken out of fluid communication with the inlet 70 and outlet 72 of the valve housing 58. The contour of the cam surface 40 maintains the first seal 28 in its second (expanded) position throughout this motion.

It is not until the handle 96 is moved beyond the non-operating, sealing position (FIG. 6) toward the releasing position (FIG. 5) that the first seal 28 is allowed to release the passageway-defining surface 14 of the heat exchanger 12.

As various changes could be made in the above constructions without departing from the scope of the invention, it is intended that all matter contained in the above description or shown in the accompanying drawing shall be interpreted as illustrative and not in a limiting sense.

We claim:

1. A mounting assembly for holding a heat exchanger of the type having a passageway-defining surface defining at least a portion of a passageway through which heat-exchanging fluid is circulated, the mounting assembly comprising:

a bracket for mounting the mounting assembly on a support;

a body mounted on the bracket, the body being adapted to be received in the passageway of the heat exchanger, the body including heat-exchanging fluid inlet and outlet passageways for circulating heat exchanging fluid through the passageway of the heat exchanger;

fixing-sealing means on the body movable between operating and releasing positions, wherein in the operating position, the fixing-sealing means is adapted for sealing against the passageway-defining surface of the heat exchanger to seal the passageway of the heat exchanger and hold the heat exchanger on the body, and in the releasing position, the fixing-sealing means is adapted for releasing the heat exchanger from the body to allow the heat exchanger to be removed from the mounting assembly or to be mounted on the mounting assembly; and valve means, operatively linked with the fixing-sealing means, for opening the heat-exchanging fluid inlet passageway when the fixing-sealing means is in its operating position, and closing the heat-exchanging fluid inlet passageway when the fixing-sealing means is in its releasing position.

2. A mounting assembly according to claim 1 wherein the fixing-sealing means further has a non-operating, sealing position between the operating position and the releasing position, wherein in the non-operating, sealing position, the fixing-sealing means is adapted for sealing against the passageway-defining surface of the heat exchanger to seal the passageway of the heat exchanger and hold the heat exchanger on the body but the valve means is closed to prevent the flow of heat-exchanging fluid in the heat-exchanging fluid inlet passageway.

3. A mounting assembly according to claim 2 wherein the valve means includes means for opening and closing the heat-exchanging fluid outlet passageway when the heat-exchanging fluid inlet passageway is opened or closed, respectively.

4. A mounting assembly according to claim 3 adapted for mounting a heat exchanger of the type having a generally cylindrical cavity defining the passageway for heat-exchanging fluid; the body of the mounting assembly being elongate and generally cylindrical, the fixing-sealing means comprising:

a ring-engaging surface on the body;

an expandable annular sealing ring co-axial with the body and engaging the ring-engaging surface of the body; and a seal-actuating member mounted on the body and trapping the expandable annular sealing ring against the ring-engaging surface of the body, the seal-actuating member being movable as the fixing-sealing means is moved between its releasing position and its non-operating, sealing position from a first position, wherein the seal-actuating member does not press the sealing ring against the ring-engaging surface sufficiently to expand the sealing ring into sealing engagement with the passageway-defining surface of the heat exchanger, to a second position, wherein the seal-actuating member presses against the sealing ring sufficiently to squeeze the annular ring against the ring-engaging surface to expand the sealing ring into sealing engagement with the passageway-defining surface of the heat exchanger, the seal-actuating member being maintained in its second position as the fixing-sealing means is moved between its non-operating, sealing position and its operating position.

5. A mounting assembly according to claim 4 wherein the fixing-sealing means further comprises a second seal, mounted on the body and spaced axially along the body from the sealing ring, for sealing engagement adjacent one end of the passageway-defining surface of the heat exchanger, the sealing ring being adapted for sealing engagement adjacent the other end of the passageway-defining surface, and means for moving the expandable sealing ring axially toward the second seal as the sealing ring is moved to its second position from its first position.

6. A mounting assembly according to claim 5 wherein the means for moving the expandable sealing ring axially toward the second seal as the sealing ring is moved to its second position from its first position comprises:

the ring-engaging surface being positioned axially along the body between the sealing ring and the second seal;

the seal-actuating member being positioned axially of the ring in the direction away from the second seal;

the seal-actuating member being movable from its first to its second positions in the direction toward the second seal; and the ring-engaging surface being generally conical, tapering outwardly in the direction toward the second seal, so that the sealing ring is pushed axially toward the second seal when it is pressed against the seal-engaging surface by the seal-actuating member.

7. A mounting assembly according to claim 6 further comprising cam means operatively linked with the seal-actuating member to move the seal-actuating member between its first and second positions.

8. A mounting assembly according to claim 7 wherein the cam means comprises a cam surface mounted on the bracket, a cam follower adapted to engage the cam surface, a linking rod, one end of which is connected to the seal-actuating member and the other end of which is connected to the cam follower, and a spring for biasing the cam follower against the cam surface, the cam surface and cam follower being adapted for rotation relative to one another from the releasing position, through the nonoperating, sealing position, to the operating position to move the seal-actuating member between its first and second positions, the cam surface being configured to hold the seal-actuating member in its second position in and between the operating position and the non-operating, sealing position.

9. A mounting assembly according to claim 8 further comprising adjustment means operatively associated with the linking rod for manually adjusting the first and second positions of the seal-actuating member.

10. A mounting assembly according to claim 9 wherein the adjustment means comprises an elongate slot formed in the linking rod adjacent the end connected to the cam follower and extending in the axial direction of the linking rod, the elongate slot receiving the cam follower to connect the cam follower to the linking arm, and an adjusting screw threadably received in the linking rod, one end of the adjusting screw engaging the cam follower to adjust the length of the linking rod between the cam follower and the seal-actuating member.

11. A mounting assembly according to claim 1 further comprising a fluid inlet and a fluid outlet in fluid communication with the valve means and having connection means for connecting to fluid supply and/or drain conduits, the valve means including bypass means for directing fluid flow directly to outlet from the inlet while bypassing the heat-exchanging inlet and outlet passageways when the valve means is closed.

12. A mounting assembly according to claim 11 wherein the valve means comprises a valve housing having a wall defining a generally cylindrical cavity, with the fluid inlet and fluid outlet being formed in the valve housing and each having an opening into the cavity, and a generally cylindrical valve member mounted in the cylindrical cavity of the valve housing for rotation relative to the valve housing, the valve member having fluid passageways opening through the cylindrical surface of the valve member and in fluid communication with the heat-exchanging fluid inlet and outlet passageways, the valve member being rotatable relative to the valve housing between an open position, wherein the openings of the fluid passageways in the valve member are aligned with the openings of fluid inlet and outlet in the valve housing so that the fluid inlet and outlet are in fluid communication with the heat-exchanging fluid inlet and outlet passageways, and a closed position, wherein the openings of the fluid passageways in the valve member are not aligned with the openings of the fluid inlet and outlet in the valve housing such that heat-exchanging fluid inlet and outlet passageways are not in fluid communication with the fluid inlet and outlet.

13. A mounting assembly according to claim 12 wherein the bypass means comprises an annular channel formed between the circumferential surface of the valve member and the wall defining the cavity of the valve housing, the channel bringing the fluid inlet and outlet into fluid communication with one another when the valve means is closed while bypassing the heat-exchanging fluid inlet and outlet passageways, the valve member including seals around the openings of the valve member for sealing against the cavity-defining wall of the valve housing.

14. A mounting assembly according to claim 13 wherein the annular channel is formed in the circumferential surface of the valve member.

15. A mounting assembly according to claim 12 wherein the body is integrally formed with the valve member.

16. A combination of a heat exchanger and a mounting assembly for holding the heat exchanger, the heat exchanger comprising:
a passageway-defining surface defining at least a portion of a passageway through which heat-exchanging fluid is circulated to allow the transfer of heat through the surface to heat or cool a different fluid on the other side of the surface; and
the mounting assembly comprising:
a bracket for mounting the mounting assembly on a support;
a body mounted on the bracket, the body being adapted to be received in the passageway of the heat exchanger, the body including heat-exchanging fluid inlet and outlet passageways for circulating heat exchanging fluid through the passageway of the heat exchanger;
fixing-sealing means on the body movable between operating and releasing positions, wherein in the operating position, the fixing-sealing means is adapted for sealing against the passageway-defining surface of the heat exchanger to seal the passageway of the heat exchanger and hold the heat exchanger on the body, and in the releasing position, the fixing-sealing means is adapted for releasing the heat exchanger from the body to allow the heat exchanger to be removed from the mounting assembly or to be mounted on the mounting assembly; and
valve means, operatively linked with the fixing-sealing means, for opening the heat-exchanging fluid inlet passageway when the fixing-sealing means is in its operating position, and closing the heat-exchanging fluid inlet passageway when the fixing-sealing means is in its releasing position.

17. The combination according to claim 16 wherein the fixing-sealing means of the mounting assembly further has a non-operating, sealing position between the operating position and the releasing position, wherein in the non-operating, sealing position, the fixing-sealing means is adapted for sealing against the passageway-defining surface of the heat exchanger to seal the passageway of the heat exchanger and hold the heat exchanger on the body but the valve means is closed to prevent the flow of heat-exchanging fluid in the heat-exchanging fluid inlet passageway.

18. The combination according to claim 17 wherein the heat exchanger is adapted for heating or cooling fluids used in cardioplegia, the combination further comprising a blood oxygenator mounted on the heat exchanger and operatively interconnected with the heat exchanger.

19. The combination according to claim 17 wherein the valve means of the mounting assembly includes means for opening and closing the heat-exchanging fluid outlet passageway when the heat-exchanging fluid inlet passageway is opened or closed, respectively.

20. The combination according to claim 19 wherein the heat exchanger has a generally cylindrical cavity defining the passageway for heat-exchanging fluid; the body of the mounting assembly being elongate and generally cylindrical and allowing manual rotation of the heat exchanger on the body, the fixing-sealing means of the mounting assembly comprising:
a ring-engaging surface on the body;
an expandable annular sealing ring co-axial with the body and engaging the ring-engaging surface of the body; and
a seal-actuating member mounted on the body and trapping the expandable annular sealing ring against the ring-engaging surface of the body, the seal-actuating member being movable as the fixing-sealing means is moved between its releasing position and its non-operating, sealing position from a first position, wherein the seal-actuating member does not press the sealing ring against the ring-engaging surface sufficiently to expand the sealing ring into sealing engagement with the passageway-defining surface of the heat exchanger, to a second position, wherein the seal-actuating member presses against the sealing ring sufficiently to squeeze the annular ring against the ring-engaging surface to expand the sealing ring into sealing engagement with the passageway-defining surface of the heat exchanger, the seal-actuating member being maintained in its second position as the fixing-sealing means is moved between its non-operating, sealing position and its operating position.

21. The combination according to claim 20 wherein the fixing-sealing means of the mounting assembly further comprises a second seal, mounted on the body and spaced axially along the body from the sealing ring, for sealing engagement adjacent one end of the passageway-defining surface of the heat exchanger, the sealing ring being adapted for sealing engagement adjacent the other end of the passageway-defining surface, and mean for moving the expandable sealing ring axially toward the second seal as the sealing ring is moved to its second position from its first position.

22. The combination according to claim 21 wherein the means of the mounting assembly for moving the expandable sealing ring axially toward the second seal as the sealing ring is moved to its second position from its first position comprises:
the ring-engaging surface being positioned axially along the body between the sealing ring and the second seal;
the seal-actuating member being positioned axially of the ring in the direction away from the second seal;
the seal-actuating member being movable from its first to its second positions in the direction toward the second seal; and
the ring-engaging surface being generally conical, tapering outwardly in the direction toward the second seal, so that the sealing ring is pushed axially toward the second seal when it is pressed against the seal-engaging surface by the seal-actuating member.

23. The combination according to claim 22 wherein the mounting assembly further comprises cam means operatively linked with the seal-actuating member to move the seal-actuating member between its first and second positions.

24. The combination according to claim 23 wherein the cam means of the mounting assembly comprises a cam surface mounted on the bracket, a cam follower adapted to engage the cam surface, a linking rod, one end of which is connected to the seal-actuating member and the other end of which is connected to the cam follower, and a spring for biasing the cam follower against the cam surface, the cam surface and cam follower being adapted for rotation relative to one another from the releasing position, through the non-operating, sealing position, to the operating position to move the seal-actuating member between its first and second positions, the cam surface being configured to hold the seal-actuating member in its second position in and between the operating position and the non-operating, sealing position.

25. The combination according to claim 24 wherein the mounting assembly further comprises adjustment means operatively associated with the linking rod for manually adjusting the first and second positions of the seal-actuating member, the adjustment means comprising an elongate slot formed in the linking rod adjacent the end connected to the cam follower and extending in the axial direction of the linking rod, the elongate slot receiving the cam follower to connect the cam follower to the linking arm, and an adjusting screw threadably received in the linking rod, one end of the adjusting screw engaging the cam follower to adjust the length of the linking rod between the cam follower and the seal-actuating member.

26. The combination according to claim 22 wherein the passageway-defining surface of the heat exchanger includes flared flanges adjacent the ends of the passageway for engaging the sealing ring and second seal, the flared flanges being flared radially outwardly relative to the longitudinal axis of the passageway.

27. The combination according to claim 16 wherein the mounting assembly further comprises a fluid inlet and a fluid outlet in fluid communication with the valve means and having connection means for connecting to fluid supply and/or drain conduits, the valve means including bypass means for directing fluid flow directly to outlet from the inlet while bypassing the heatexchanging inlet and outlet passageways when the valve means is closed.

28. The combination according to claim 27 wherein the valve means of the mounting assembly comprises a valve housing having a wall defining a generally cylindrical cavity, with the fluid inlet and fluid outlet being formed in the valve housing and each having an opening into the cavity, and a generally cylindrical valve member mounted in the cylindrical cavity of the valve housing for rotation relative to the valve housing, the valve member having fluid passageways opening through the cylindrical surface of the valve member and in fluid communication with the heat-exchanging fluid inlet and outlet passageways, the valve member being rotatable relative to the valve housing between an open position, wherein the openings of the fluid passageways in the valve member are aligned with the openings of fluid inlet and outlet in the valve housing so that the fluid inlet and outlet are in fluid communication with the heat-exchanging fluid inlet and outlet passageways, and a closed position, wherein the openings of the fluid passageways in the valve member are not aligned with the openings of the fluid inlet and outlet in the valve housing such that heatexchanging fluid inlet and outlet passageways are not in fluid communication with the fluid inlet and outlet.

29. The combination according to claim 28 wherein the bypass means comprises an annular channel formed between the circumferential surface of the valve member and the wall defining the cavity of the valve housing, the channel bringing the fluid inlet and outlet into fluid communication with one another when the valve means is closed while bypassing the heat-exchanging fluid inlet and outlet passageways, the valve member including seals around the openings of the valve member for sealing against the cavity-defining wall of the valve housing.

30. The combination according to claim 29 wherein the annular channel is formed in the circumferential surface of the valve member.

31. The combination according to claim 28 wherein the body is integrally formed with the valve member.

32. A mounting assembly for holding a heat exchanger of the type adapted for heating or cooling fluid used in cardioplegia, having a passageway-defining surface defining at least a portion of a passageway through which heat-exchanging fluid is circulated, the mounting assembly comprising:

a bracket for mounting the mounting assembly on a support;

a body mounted on the bracket, the body being adapted to be received in the passageway of the heat exchanger, the body including heat-exchanging fluid inlet and outlet passageways for circulating heat-exchanging fluid through the passageway of the heat exchanger;

an expandable seal on the body expandable from a first position to a second position, wherein in the first position, the expandable seal is not expanded so that the expandable seal is adapted to release the heat exchanger from the body to allow the heat exchanger to be removed from the mounting assembly or to be mounted on the mounting assembly, and in the second position, the expandable seal is expanded so that the expandable seal is adapted to seal against the passageway-defining surface of the heat exchanger to seal the passageway of the heat exchanger and hold the heat exchanger on the body;

a valve for opening and closing the heat-exchanging fluid inlet passageway; and a single manually operable means for expanding the expandable seal from its first to its second position and for opening and closing the valve such that the valve is always closed when the expandable seal is in its first position.

33. A mounting assembly for holding a heat exchanger of the type adapted for heating or cooling fluid used in cardioplegia, having a passageway-defining surface defining at least a portion of a passageway through which heat-exchanging fluid is circulated, the mounting assembly comprising:

a bracket for mounting the mounting assembly on a support;

a body mounted on the bracket, the body being adapted to be received in the passageway of the heat exchanger, the body including heat-exchanging fluid inlet and outlet passageways for circulating heat-exchanging fluid through the passageway of the heat exchanger;

an expandable seal on the body expandable from a first position to a second position, wherein in the first position, the expandable seal is not expanded so that the expandable seal is adapted to release the heat exchanger from the body to allow the heat exchanger to be removed from the mounting assembly or to be mounted on the mounting assembly, and in the second position, the expandable seal is expanded so that the expandable seal is adapted to seal against the passageway-defining surface of the heat exchanger to seal the passageway of the heat exchanger and hold the heat exchanger on the body;

a valve for opening and closing the heat-exchanging fluid inlet passageway; and manually operable means for expanding the expandable seal from its first to tis second position and for opening and closing the valve such that the valve is always closed when the expandable seal is in its first position;

the manually operable means (a) closing the valve before the expandable seal is allowed to move from its second position toward its first position, and (b) expanding the expandable seal to its second position from its first position before opening the valve; and the valve opening and closing the heat-exchanging fluid outlet passageway when the heat-exchanging fluid inlet passageway is opened or closed, respectively.

34. A mounting assembly according to claim 33 adapted for mounting a heat exchanger of the type having a generally cylindrical cavity defining the passageway for heat-exchanging fluid; the body of the mounting assembly being elongate and generally cylindrical and adapted to allow manual rotation of the heat exchanger on the body, the expandable seal comprising an expandable annular sealing ring co-axial with the body, the manually operable means including:

a ring-engaging surface on the body; and a seal-actuating member mounted on the body and trapping the expandable annular sealing ring against the ring-engaging surface of the body, the seal-actuating member being movable axially relative to the body to move the sealing ring between the first position, wherein the seal-actuating member does not press the sealing ring against the ring-engaging surface sufficiently to expand the sealing ring into sealing engagement with the passageway-defining surface of the heat exchanger, to the second position, wherein the seal-actuating member presses against the sealing ring sufficiently to squeeze the sealing ring against the ring-engaging surface to expand the sealing ring into sealing engagement with the passageway-defining surface of the heat exchanger.

35. A mounting assembly according to claim 34 further comprising a second seal, mounted on the body and spaced axially along the body from the sealing ring, for sealing engagement adjacent one end of the passageway-defining surface of the heat exchanger, the sealing ring being adapted for sealing engagement adjacent the other end of the passageway-defining surface, the ring-engaging surface being positioned axially along the body between the sealing ring and the second seal;

the seal-actuating member being positioned axially of the ring in the direction away from the second seal;

the seal-actuating member being movable from the first to its second positions in the direction toward the second seal; and the ring-engaging surface being generally conical, tapering outwardly in the direction toward the second seal, so that the sealing ring is pushed axially toward the second seal when it is pressed against the seal-engaging surface by the seal-actuating member.

36. A mounting assembly according to claim 35 wherein the manually operable means further comprises a cam surface mounted on the bracket, a cam follower adapted to engage the cam surface, a linking rod, one end of which is connected to the seal-actuating member and the other end of which is connected to the cam follower, and a spring for biasing the cam follower against the cam surface, the cam surface and cam follower being adapted for rotation relative to one another from a releasing position, through a non-operating, sealing position, to an operating position to move the seal-actuating member between the first and second positions, the cam surface being configured to hold the seal-actuating member in its second position in and between the operating position and the non-operating, sealing position, the manually operable means opening and closing the valve as the cam surface and cam follower are rotated between their operating and nonoperating, sealing positions, the manually operable means further comprising a handle for manually rotating one of the cam follower and cam surface relative to the other of the cam follower and cam surface.

37. A mounting assembly according to claim 36 wherein manually operable means includes an adjustment mechanism comprising an elongate slot formed in the linking rod adjacent the end connected to the cam follower and extending in the axial direction of the linking rod, the elongate slot receiving the cam follower to connect the cam follower to the linking arm, and an adjusting screw threadably received in the linking rod, one end of the adjusting screw engaging the cam follower to adjust the length of the linking rod between the cam follower and the seal-actuating member.

38. A mounting assembly according to claim 32 further comprising a fluid inlet and a fluid outlet in fluid communication with the valve and having connectors for connecting to fluid supply and/or drain conduits, the valve directing fluid flow directly to outlet from the inlet while bypassing the heat-exchanging inlet and outlet passageways when the valve is closed.

39. A mounting assembly for holding a heat exchanger of the type adapted for heating or cooling fluid used in cardioplegia, having a passageway-defining surface defining at least a portion of a passageway through which heat-exchanging fluid is circulated, the mounting assembly comprising:
  a bracket for mounting the mounting assembly on a support;
  a body mounted on the bracket, the body being adapted to be received in the passageway of the heat exchanger, the body including heat-exchanging fluid inlet and outlet passageways for circulating heat-exchanging fluid through the passageway of the heat exchanger;
  an expandable seal on the body expandable from a first position to a second position, wherein in the first position, the expandable seal is not expanded so that the expandable seal is adapted to release the heat exchanger from the body to allow the heat exchanger to be removed from the mounting assembly or to be mounted on the mounting assembly, and in the second position, the expandable seal is expanded so that the expandable seal is adapted to seal against the passageway-defining surface of the heat exchanger to seal the passageway of the heat exchanger and hold the heat exchanger on the body;
  a valve for opening and closing the heat-exchanging fluid inlet passageway;
  manually operable means for expanding the expandable seal from its first to it's second position and for opening and closing the valve such that the valve is always closed when the expandable seal is in its first position; and
  a fluid inlet and a fluid outlet in fluid communication with the valve and having connectors for connecting to fluid supply and/or drain conduits, the valve directing fluid flow directly to outlet from the inlet while bypassing the heat-exchanging inlet and outlet passageways when the valve is closed;
  the valve comprising a valve housing having a wall defining a generally cylindrical cavity, with the fluid inlet and fluid outlet being formed in the valve housing and each having an opening into the cavity, and a generally cylindrical valve member mounted in the cylindrical cavity of the valve housing for rotation relative to the valve housing, the valve member having fluid passageways opening through the cylindrical surface of the valve member and in fluid communication with the heat-exchanging fluid inlet and outlet passageways, the valve member being rotatable relative to the valve housing between an open position, wherein the openings of the fluid passageways in the valve member are aligned with the openings of fluid inlet and outlet in the valve housing so that the fluid inlet and outlet are in fluid communication with the heat-exchanging fluid inlet and outlet passageways, and a closed position, wherein the openings of the fluid passageways in the valve member are not aligned with the openings of the fluid inlet and outlet in the valve housing such that heat-exchanging fluid inlet and outlet passageways are not in fluid communication with the fluid inlet and outlet, the valve further including an annular channel formed between the circumferential surface of the valve member and the wall defining the cavity of the valve housing, the channel brining the fluid inlet and outlet into fluid communication with one another when the valve means is closed while bypassing the heatexchanging fluid inlet and outlet passageways, the valve member including seals around the openings of the valve member for sealing against the cavity-defining wall of the valve housing.

40. A mounting assembly according to claim 39 wherein the annular channel is formed in the circumferential surface of the valve member.

41. A heat exchanger for heating or cooling blood or cardioplegia solution by transferring heat between the blood or solution and heat-exchanging fluid, the heat exchanger being adapted to be mounted on a mounting assembly of the type comprising a bracket for mounting the mounting assembly on a support, a body mounted on the bracket, the body defining an axis, expandable fixing-sealing means on the body movable between operating and releasing positions, wherein in the operating position the fixing-sealing means is expanded relative to the releasing position to hold and seal the heat exchanger on the mounting assembly, and a seal on the body axially spaced from the fixing-sealing means; the heat exchanger comprising:
  a housing;
  a fluid barrier in the housing having an inner surface defining a passageway for circulating heatexchanging fluid, the passageway having opposite ends and being open at one end thereof for receiving the body of the mounting assembly; and
  flared means extending from each end of the fluid barrier and flaring radially outwardly relative to the passageway adapted for engaging the fixing-sealing means of the mounting assembly to allow the fixing-sealing means to apply a force to the flared means to move the heat exchanger axially along the body such that the flared means at the opposite end of the passageway sealingly engages the seal, whereby the opposite ends of the passageway are sealed by the fixing-sealing means and the seal of the heat exchanger.

42. A heat exchanger according to claim 41 wherein the flared means comprises two flared flanges, each extending from a respective end of the fluid barrier, the flared flanges flaring outwardly relative to the passageway, the passageway being open at both opposite ends.

43. A heat exchanger according to claim 42 wherein the flared flanges are flared outwardly at an angle of approximately 24 degrees relative to the axis of the passageway.

* * * * *

UNITED STATES PATENT AND TRADEMARK OFFICE
CERTIFICATE OF CORRECTION

PATENT NO. : 5,255,734

DATED : October 26, 1993

INVENTOR(S) : Ronald J. Leonard, David B. Maurer and Erin J. Lindsay

It is certified that error appears in the above-indentified patent and that said Letters Patent is hereby corrected as shown below:

Abstract [57], line 4, "heatexchanging" should read --heat-exchanging--.

Col. 5, line 5, "2" should read --32--.

Col. 7, line 42, after "surface" insert --14--.

Col. 10, line 54, "(FIG. 4. " should read --(FIG. 4).--.

Col. 10, line 59, "longitudi,nally" should read --longitudinally--.

Col. 11, line 19, "or" should read --of--.

Col. 11, line 20, "-5 inches" should read --5 inches--.

Col. 11, line 67, "12" should read --10--.

Col. 12, line 58, "tne" should read --the--.

Col. 17, line 22, "mean" should read --means--.

Col. 18, line 48, "heatexchanging" should read --heat-exchanging--.

UNITED STATES PATENT AND TRADEMARK OFFICE
CERTIFICATE OF CORRECTION

PATENT NO. : 5,255,734
DATED : October 26, 1993
INVENTOR(S) : Ronald J. Leonard, David B. Maurer and Erin J. Lindsay It is certified that error appears in the above-indentified patent and that said Letters Patent is hereby corrected as shown below:

Col. 19, line 63, "tis" should read --its--.

Col. 22, lines 54-55, "heatexchanging" should read --heat-exchanging--.

Signed and Sealed this

Eleventh Day of April, 1995

Attest:

BRUCE LEHMAN

Attesting Officer

Commissioner of Patents and Trademarks